United States Patent [19]

Meals

[11] 4,212,300
[45] Jul. 15, 1980

[54] RUBBER BAND POWERED PISTON VALVE ASPIRATOR

[76] Inventor: Roy A. Meals, 10376 Keswick Ave., Los Angeles, Calif. 90064

[21] Appl. No.: 875,401

[22] Filed: Feb. 6, 1978

[51] Int. Cl.² ............................................. A61M 1/00
[52] U.S. Cl. .................................. 128/276; 251/321; 267/74; 15/344
[58] Field of Search ....................... 128/274, 276, 278; 206/805; 137/DIG. 4; 251/320, 321; 267/69, 73, 74; 222/511, 513; 15/344; 124/17, 21

[56] References Cited

U.S. PATENT DOCUMENTS

| 2,812,765 | 11/1957 | Tofflemire | 128/276 |
| 3,162,444 | 12/1964 | Jackson et al. | 124/17 |
| 3,297,206 | 1/1967 | Scholle | 222/105 |
| 3,810,471 | 5/1974 | Truhan | 128/276 |

FOREIGN PATENT DOCUMENTS 183558  7/1922  United Kingdom ..................... 128/276

OTHER PUBLICATIONS

University Physics, Third Edition, Addison Wesley Publishing Co. Inc. Reading, Mass. Rec'd 12/22/66.

*Primary Examiner*—Robert W. Michell
*Assistant Examiner*—J. L. Kruter

[57] ABSTRACT

The invention is an improved aspirator for use in medical procedures. The aspirator is provided with a rubber band powered piston control valve that maintains the valve in the off position. When operated to the on position by a user, the rubber band is placed in tension mode so that when released by the user the rubber band returns the valve to the off position. The rubber band powered piston valve aspirator is simple to disassemble without tools for cleaning and sterilization.

2 Claims, 5 Drawing Figures

RUBBER BAND POWERED PISTON VALVE ASPIRATOR

BACKGROUND AND SUMMARY OF THE INVENTION

The invention relates to aspirators and in particular to aspirators used in medical procedures. The aspirators used in medical procedures (surgical aspirators) are used as suction devices for the removal of various body fluids during medical procedures, such as surgery.

Existing aspirators are equipped with various types of valves that are spring loaded, are difficult to disassemble, often requiring tools for the disassembly, and are difficult to clean prior to sterilization. Other aspirator valves are not assured an instantaneous suction when opened or an instantaneous cut-off when closed.

The present invention has a very simple thumb or finger button for operation of the valve. The valve is powered by an ordinary rubber band that maintains the valve in the off position. When the valve is operated to produce a suction, the rubber bands are placed in tension so that when the valve is released the rubber band returns the valve to the off position.

The assembly of the valve is very simple and can be performed without tools. Likewise, the valve can be disassembled without tools.

It is, therefore, an object of the invention to provide an aspirator that has a rubber band powered valve.

It is a further object of the invention to provide an aspirator that is simple to assemble without tools.

It is another object of this invention to provide an aspirator that is simple to disassemble without tools.

It is a further object of this invention to provide an aspirator that is easily cleaned.

It is yet another object of this invention to provide an aspirator that is easy to sterilize.

Further objects and advantages of the invention will become more apparent in light of the following description of the preferred embodiments.

DESCRIPTION OF THE PREFERRED EMBODIMENTS

Figure 1:
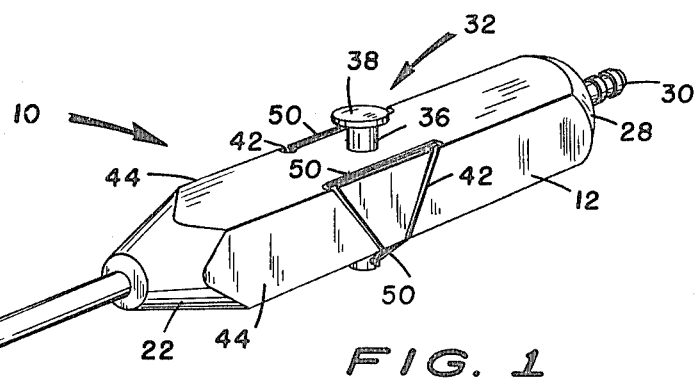
FIG. 1 is a perspective view of the assembled aspirator showing the assembled valve and the rubber band that powers the valve.

Referring to the drawings and particularly to FIG. 1, an improved rubber band powered piston valve aspirator is shown at 10.

The aspirator 10 is seen to consist of the valve body 12, a male connection 30 for connection to a vacuum or suction system, a probe tube 16, a probe tip 26 with entry ports therein, a valve piston 36 for control and with a finger or thumb button 38, and a rubber band 50 for maintaining the valve piston 36 in the off position.

Figure 2:
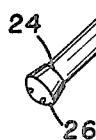
FIG. 2 is a longitudinal cross section through the valve, with the rubber band removed and the valve piston in disassembled position.
Figure 3:
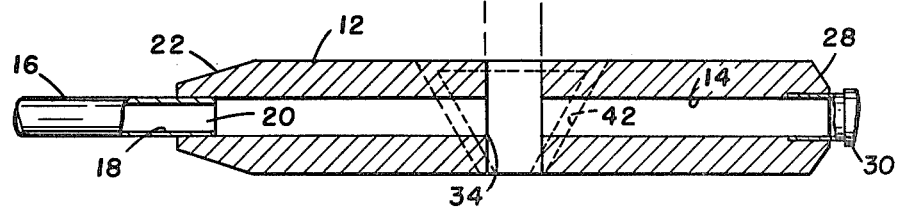
FIG. 3 is an enlarged view of the valve showing the rubber band in position and showing a partial section at the valve piston in the off position.
Figure 4:
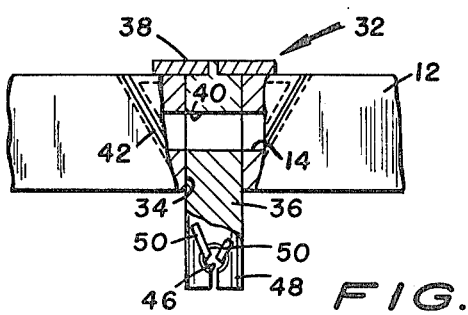
FIG. 4 is a partial section of the valve with the valve piston in the on position.

The valve assembly 32 in FIG. 1 is shown in longitudinal cross section in FIG. 2, and in partial section in FIG. 3 with the valve piston 36 in off position, and in partial section in FIG. 4 with the valve piston 36 in the open position.

Returning now to FIG. 1, the rubber band 50 can be seen assembled in the grooves 42 and passing down under the valve body 12 through the end of valve piston 36. In FIG. 2 at the lower end 48 of valve piston 36, the special slot for the rubber band 50 to pass through can be seen. The rubber band 50 is passed up through the narrow portion of the special slot 46 until it is in the round part of the special slot 46. The rubber band 50 can be seen passing through round part of special slot 46 in FIGS. 3 and 4 at the lower end 48 of the valve piston 36.

In FIG. 3 the rubber band 50 is in the contracted mode which holds the valve piston 36 in the off position. The passage port 40 through the valve piston 36 can be seen in the off position in relation to the passageway 14 through the valve body 12.

Suction communication is made through the communication of the entry ports in the probe tip 26, the interior passageway 18 of probe 16, the passageway 14 in the valve body 12, and the male connector 30.

In FIG. 4 the rubber band 50 is in the tension mode as the finger or thumb button 38 is pressed down, which in turn moves the valve piston 36 (to which thumb button 38 is attached) downward so that the passage port 40 through the valve piston 36 is aligned with the passageway 14 which runs longitudinally through the valve body 12. Then the suction or vacuum system flexible rubber or plastics tubings connected to the aforesaid male connection 30 can suck in whatever body fluid the aforementioned probe 16 is directed to, the body fluid entering through the entry ports in the probe tip 26 on the end 24 of the probe 16. When the finger of thumb button 38 is released the rubber band 50 (in tension) will contract and return the valve piston 36 to the off position as shown in FIG. 3 and the suction action is cut off.

The shape of the valve body 12 in FIG. 1 shows four flat sides 44, a tapered forward end 22, and a rounded back end 28. It should be understood that other configurations such as round, hexagonal, octagonal, or similar shapes, and blunt or flat ends is within the scope and intent of this invention. It is also to be noted that the somewhat arcuate shape of the probe 16 may also be straight or bent in a more severe radius, but such variations are also within the scope and intent of this invention.

The aspirator body 12 and parts, except for the rubber band 50, are metal, but it should be understood that other suitable material such as a plastics or glass could be used. Any such variation in materials is also within the scope and intent of this invention.

In FIG. 2 the configuration of the grooves 42 for mounting said rubber-bands 50 can be seen in a side view. Also, the detail of the passage port 40, the passageway 14, and the assembly of the male connection 30 and the probe 16 to the valve body 12 can be seen clearly in FIG. 2. The interior passageway 18 of the probe 16 is shown clearly at the probe 16 end 20. The valve piston 36 slideably disposed in moves up and down in the piston cylinder 34 in the valve body 12, which is perpendicular to the passageway 14.

Figure 5:
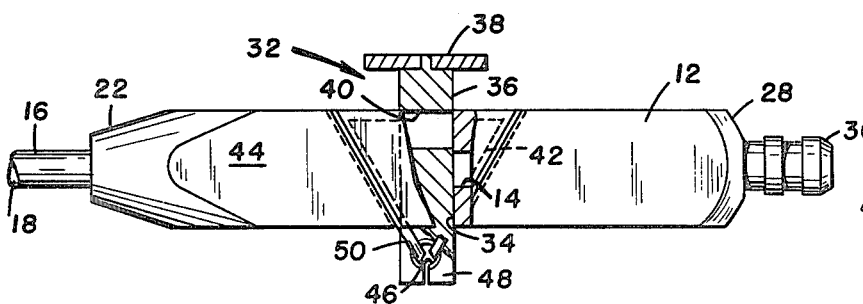
FIG. 5 is a partial perspective view of the valve body showing grooves for rubber band.
Figure 5:
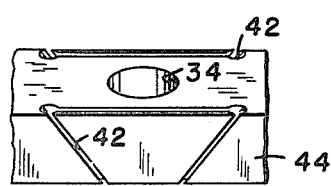

In FIG. 5 the top part of piston cylinder 34 is in the valve body 12. The grooves 42 for the rubber band 50 can also be seen in FIG. 5, note raised edge that creates the groove 42 on the top side of the valve body 12. The raised edge is between the groove 42 and the face 44 of the valve body 12. The raised edge retains the rubber band 50 on each side of the valve body 12 when the rubber band 50 is assembled in the grooves 42 and through the aforementioned slot 46 in the valve piston 36. The simplicity of disassembly without tools by removal of the rubber band 50 and then the valve piston 36, and the simplicity of the reassembly in the reverse order without tools should be noted. In those aspirators using a compression spring for the operation, parts with screw threads to assemble the device or machine screws to hold the parts in place, requiring tools for assembly and disassembly.

The ease of cleaning the simple parts before sterilization should also be noted. In other aspirators there are numerous parts and difficult places to clean properly before sterilization. The aspirator 10 is fully steam autoclavable for sterilization.

The aforementioned features of assembly, disassembly, cleaning, and simple operation are the novel and unique features of this invention that are not present in other aspirators. The mechanism of this invention can also be assembled in existing standard surgical aspirator systems. Other uses for this simple rubber band powered valve arrangement may also be made, but such other uses are within the scope and intent of this invention.

The axis of the slot 46 is perpendicular to the passage port 40. When the rubber band 50 is assembled through the slot 46 it maintains the alignment of the passage port 40 with the passage 14.

In assembling the rubber band 50 it is looped over and into the groove 42 on one side of the valve body 12, passed under the valve body 12 and up the other side of the valve body 12 and then looped over and into the groove 42 on the top. The valve piston 36 is then inserted in the piston cylinder 34 at the top of the valve body 12 and pushed through to the other side or bottom. The rubber band 50 (both strands) are then inserted in the slot 46.

Note that when the rubber band 50 holds the valve piston 36 in the off position, a solid portion of the valve piston 36 occludes the passageway 14. When the finger or thumb button 38 is depressed it bottoms out when its underside touches the top of the valve body 12; at this point the passage port 40 in the valve piston 36 is aligned with the passageway 14 in the valve body 12.

In holding the aspirator 10 for operation the valve body 12 serves as a handle and the thumb of the hand comes naturally to the button 38 for operation. For those who find it more convientent, a finger may be used instead of the thumb to operate the button 38.

It is to be noted that the grooves 42 may be rounded at the bottom or cut square, so long as the groove 42 is large enough in cross section to accept the cross section size of the rubber band 50. When the rubber band 50 is installed it prevents the valve piston 36 from falling out because the rubber band 50 is inserted in the slot 46. Although the rubber band 50 is in the contracted mode when the valve piston 36 is in the off position, there is sufficient tension within the rubber band 50 to prevent it from coming out of the grooves 42 on the top side of the valve body 12. The course of the grooves 42 disposed down the sides of the valve body 12 and across the top of the valve body 12 approximates a triangle as seen from the sides in FIG. 3.

It is to be noted that the shapes of the finger or button 38, the grooves 42, and the keyslot 46 may be changed and still fall within the scope of the invention.

Accordingly, modifications and variations to which the invention is susceptible may be practiced without departing from the scope of the appended claims.

What I claim is:

1. A surgical aspirator, comprising:
   a body means with a passageway therethrough;
   a control valve means installed in said body means to control suction flow therethrough, said control valve means consisting of a valve piston with a passageway therethrough arranged perpendicularly to cylindrical sides thereof for communication with said passageway in said body means when said valve piston is in an on position, said valve piston having a slot in the bottom end thereof for anchoring a power means, a piston cylinder in said body means, in which said valve piston is disposed, and so situated in said body means so that passageway through said valve piston may be aligned with said passageway in said body means, and a thumb button attached to top of said valve piston for depressing the valve piston;
   a probe means connected to one end of said body means, the interior passageway of said probe means communicating with the interior passageway through said body means, said probe means having a tip on the end thereof, said tip having at least one entry port therein, said entry port communicating with the interior passageway of said probe means;
   a male connection means connected to one end of said body means opposite to end to which said probe means is connected, the interior of said male connection means communicating with the interior passageway of said body means, with a vacuum or suction system connected to said male connection; and
   a power means for operation of said control valve means, said power means being a rubber band, said rubber band power means being attached to said body means, said body means having a system of grooves on the exterior thereof in a configuration to mount said power means, said rubber band power means being attached to a first edge of said body means, then passing down a first side of said body means, passing through a slot in bottom of said valve piston, then passing up a second side of said body means, and being attached to a second edge of said body means.

2. A surgical aspirator, comprising:
   a body means with a passageway therethrough, said body means having a system of grooves on the exterior in a configuration to mount and guide a power means thereon,
   a control valve means installed in said body means to control suction flow therethrough;
   a probe means connected to one end of said body means, the interior passageway of said probe means communicating with the interior passageway through said body means;
   a male connection means connected to one end of body means opposite to end to which said probe means is connected, the interior of said male connection means communicating with the interior passageway of said body means;
   a power means for operation of said control valve means;

said power means is of a rubber band type and said control valve means consists of:
- a valve piston with a passageway therethrough perpendicular to cylindrical sides thereof for communication with said passageway in said body means when said valve piston is in on position, said valve piston having a slot in the bottom end thereof for anchoring said rubber band power means;
- a piston cylinder in said body means, in which said valve piston is disposed, and so situated in said body means so that passageway through said valve piston may be aligned with said passageway in said body means; and
- a thumb button attached to top of said valve piston for depressing valve piston;

said rubber band means is a standard rubber band approximately two inches in diameter;

said rubber band power means is attached to one edge of said valve body means, passes down side of said valve body, passes through a slot in bottom of said valve piston, then passes up opposite side of said valve body and attaches to edge of said valve body means.

* * * * *